United States Patent
Pivarnik et al.

(10) Patent No.: US 6,630,355 B1
(45) Date of Patent: Oct. 7, 2003

(54) MAGNETIC FOCUSING IMMUNOSENSOR FOR THE DETECTION OF PATHOGENS

(75) Inventors: Philip Pivarnik, Narragansett, RI (US); He Cao, Kingston, RI (US); Stephen V. Letcher, Kingston, RI (US); A. Garth Rand, Kingston, RI (US)

(73) Assignees: The Board of Governors for Higher Education State of Rhode Island; Providence Plantation, Providence, RI (US)

( * ) Notice: Subject to any disclaimer, the term of this patent is extended or adjusted under 35 U.S.C. 154(b) by 18 days.

(21) Appl. No.: 09/753,201

(22) Filed: Jan. 2, 2001

Related U.S. Application Data

(62) Division of application No. 09/438,081, filed on Nov. 5, 1999, now Pat. No. 6,254,830.

(51) Int. Cl.⁷ .............................................. G01N 21/00
(52) U.S. Cl. ..................... 436/164; 436/172; 436/530; 436/532; 436/536; 436/166; 436/546; 436/800; 436/805; 436/501; 436/75; 436/65; 436/79.81; 436/85; 436/86; 436/806; 436/533; 436/584; 435/7.5; 435/7.1; 435/287.1; 435/288.7; 435/176; 435/283.1; 435/289.1; 435/290; 435/7.33; 435/7.34; 435/7.35; 356/300; 356/244; 356/301; 356/303; 356/319; 356/326; 356/311; 385/123; 422/82.11
(58) Field of Search ................................ 436/164, 172, 436/530, 532, 536, 800, 166, 805, 546, 74, 75, 501, 65, 79.81, 85, 86, 806, 533, 584; 435/7.5, 7.1, 287.1, 288.7, 176, 283.1, 289.1, 290.1, 7.33, 7.34, 7.35; 356/300, 244, 301, 303, 319, 326, 311; 385/123; 422/82.11

(56) References Cited

U.S. PATENT DOCUMENTS

| | | | |
|---|---|---|---|
| 4,891,324 A | * | 1/1990 | Pease et al. |
| 5,076,950 A | * | 12/1991 | Ullman et al. |
| 5,126,376 A | * | 6/1992 | Fish et al. ................... 436/531 |
| 5,279,936 A | * | 1/1994 | Vorpahl ......................... 435/6 |
| 5,359,681 A | * | 10/1994 | Jorgenson et al. ............. 385/12 |
| 5,374,395 A | * | 12/1994 | Robinson et al. ............. 422/64 |
| 5,496,700 A | * | 3/1996 | Ligler et al. ................. 435/7.1 |
| 5,536,644 A | * | 7/1996 | Ullman et al. |
| 5,786,151 A | * | 7/1998 | Sanders |
| 5,824,478 A | * | 10/1998 | Muller .......................... 435/6 |
| 5,837,196 A | | 11/1998 | Pinkel et al. |
| H1775 H | * | 1/1999 | Ligler et al. ............... 435/7.32 |
| 5,869,701 A | * | 2/1999 | Park et al. ................... 549/283 |
| 5,938,595 A | * | 8/1999 | Glass et al. |
| 5,952,236 A | * | 9/1999 | Thompson et al. |
| 5,965,142 A | * | 10/1999 | Dillon et al. ............. 424/269.1 |
| 5,982,959 A | * | 11/1999 | Hopenfeld ................... 385/12 |
| 6,103,535 A | * | 8/2000 | Pilevar et al. .............. 436/518 |
| 6,136,611 A | * | 10/2000 | Saaski et al. ............... 435/527 |
| 6,140,138 A | * | 10/2000 | Bard et al. |
| 6,146,593 A | * | 11/2000 | Pinkel et al. .............. 422/68.1 |
| 6,163,714 A | * | 12/2000 | Stanley et al. .............. 600/316 |
| 6,197,258 B1 | * | 3/2001 | Thompson et al. ...... 422/82.07 |
| 6,210,910 B1 | * | 4/2001 | Walt et al. .................. 435/7.32 |
| 6,225,046 B1 | * | 5/2001 | Vesey et al. |

\* cited by examiner

Primary Examiner—Christopher L. Chin
Assistant Examiner—Pensee T. Do
(74) Attorney, Agent, or Firm—Samuels, Gauthier & Stevens, LLP

(57) ABSTRACT

A magnetic focusing immunosensor for the detection of pathogens comprising a laser, an exciting fiber and a collecting fiber, a fiber optic magnetic probe in communication with the collecting and exciting fibers and means for detecting, collecting and measuring fluorescent signals in communication with the collecting fiber. The probe and the collecting and exciting fibers are configured to focus paramagnetic microspheres attached to antigen/antibody/optically labeled complexes in a predetermined pattern in the field of view of the collecting fiber while blocking background interference.

6 Claims, 3 Drawing Sheets

NOTE: For Current Setup,
h=0 mm,
d=0.8 mm,
2r =0.5 mm,
alpha=18.2 degree

MAGNETIC FOCUSING IMMUNOSENSOR FOR THE DETECTION OF PATHOGENS

This application is a divisional of U.S. Patent application Ser. No. 09/438,081 filed on Nov. 5, 1999, now U.S. Pat. No. 6, 254,830.

STATEMENT REGARDING FEDERALLY SPONSORED RESEARCH OR DEVELOPMENT

The U.S. Government has a paid up license in this invention and the right in limited circumstances to require the patent owner to license others on reasonable terms as provided for by the terms of Grant No. 97-352014480 from the US Department of Agricultural National Research Initiative Competitive Grant Program on Food Safety and Contract No. DAAK6095C2035 from the US Army Soldier Systems Command/Natick.

BACKGROUND OF THE INVENTION

1. Field of the Invention

A fiber-optic biosensor for assaying an analyte of interest.

2. Description of the Related Art

Concern over virulent pathogens contaminating the food supply has the potential to put large segments of the population at risk. The scientific estimates project that between 24 million and 81 million people become ill from foodborne diarrheal disease each year in the United States. The impact of this food contamination costs between $5 billion and $17 billion in medical care costs and lost productivity. Most toxicologists and food scientists agree these figures probably represent about 75 % of the whole food safety risks, confirming that microbial pathogens are considered a serious hazard.

The impact due to Salmonella has been estimated at >$4 billion from more than 3 million cases/year. The lack of success in effectively controlling the growth of these pathogens in foods suggests that the best approach would be early and rapid detection. Approximately 5 million analytical tests are performed annually in the U.S., which makes detection a high priority for diagnostic technology.

Traditional methods to identify and quantitate contaminants in foods include physicochemical, biological and serological tests. Most of these approaches lack sufficient sensitivity, selectivity, and take days to perform. There have been many attempts to provide faster and convenient detection methods. Most of these detection systems, although referred to as "rapid methods", still rely on culturing procedures to selectively amplify microbial populations.

The development of food immunoassays to improve this process has provided increased speed, simplicity, and effectiveness. However, these current procedures are expensive, usually require an enrichment/concentration step and still require hours to days for a final result. The adaptation of this immunoassay technology to biosensors has the potential to take immunoassays into the realm of rapid and reusable biosensors. The application of biosensors to the detection of Salmonella has the potential to contribute directly to the production and processing of safer and healthier food.

Biosensors are analytical devices which incorporate biologically active material in intimate contact with a transduction element to selectively and repeatedly detect analytes in products like food and food raw materials. The effective development of biosensors has become multidisciplinary, relying on biochemistry and biotechnology to provide the sensing elements through immobilization techniques and membrane technology, but also requires expertise in microelectronics, optical, acoustical and advanced signal processing. This dramatic combination can be effectively applied in the area of food safety, for the elimination of serious health risks by rapid detection of specific pathogens.

A compact fiber-optic evanescent-wave biosensor system which features an all-fiber optical design and red semiconductor-laser excitation has been developed. C. Zhou, P. Pivarnik, S. Auger, A Rand and S. Letcher, "A compact fiber optic immunosensor for Salmonella based on evanescent wave excitation", Sensors and Actuators B 42, pp. 169–175, 1997. Tapered fiber tips with immobilized antibodies for Salmonella attached were studied in different shapes and treatments and optimized. The system response for Salmonella concentration was established and could determine as low as $10^4$ colony forming units (CFU/mL) in 1 hour with a sandwich immunoassay format. Acoustic enhancement of the fiber-optic biosensor with ultrasonic manipulation of suspended particles has been shown to be an effective way to increase the sensitivity. C. Zhou, P Pivarnik, A. Rand, and S. Letcher, "Acoustic standing-wave enhancement of a fiber optic Salmonella biosensor", Biosensors and Bioelectronics 13, pp 495–500, 1998. Polystyrene microspheres (6-mm diameter) coated with immobilized antibodies were allowed to capture the antigens (Salmonella), which in turn captured antibodies labeled with fluorescent dye molecules. Then the entire structure was moved to the center of the acoustic cell, where the optical fiber with its cladding removed was located. The fluorescent signal was greatly increased over the signal without acoustic positioning. Multiple use of the system was also rapid because the fiber tip could be reused indefinitely (no antibodies were attached)— the flow cell just nee to be flushed out with a buffer solution and was ready for reuse.

Although the use of evanescent wave and tapered fibers provided average sensitivity and measurement potential, these systems did not achieve rapid and direct pathogen detection for food use. Currently the best available commercial system has a sensitivity of $10^4$ Colony Forming Units/ml (CFU/ml) and measurement potential of $10^7$ to $10^8$ CFU/ml. The time to complete an assay is usually 3 to 4 hours.

SUMMARY OF THE INVENTION

The present invention comprises a fiber optic biosensor and method for the detection of pathogens, i.e. bacteria, viruses and/or toxins. The fiber-optic biosensor comprises a laser in communication with an excitation fiber. The excitation fiber is in communication with a collection fiber and the excitation and collection fibers are in communication with a magnetic focusing probe. The collection fiber is in communication with a transmission fiber which is in communication with means for detecting, collecting and measuring fluorescent signals. The present invention reduces the background fluorescence from unbound antibodies and eliminates several rinsing steps thereby resulting in a simple rapid assay.

Broadly the invention comprises magnetic focusing of paramagnetic microspheres with a fiber optic biosensor. Microspheres with immobilized antibodies interact throughout the analyte containing the target antigens, which, in turn, capture fluorescent-labeled antibodies in a standard sandwich assay. The bound antigen/antibody/fluorescent antibody complexes are magnetically attracted to the magnetic focusing probe of the fiber optic biosensor which contains the sensing volume of the excitation and collection fibers, while the uncaptured labeled fluorescent antibodies remain in bulk solution thereby reducing background fluorescence.

In contrast to the prior art fiber-optic immunoassays that are acoustically focused and have several steps for detection, the present invention provides an inunnoassay that uses magnetic focusing and only requires three steps, specifically; 1) immunocapture and labeling, 2) rinsing and 3) focusing and measurement of fluorescent signal. Furthermore, the fiber-optic immunosensor of the present invention is more efficient than prior art fluorescent immunosensors because prior art fluorescent immunosensors do not concentrate the bound antigen/antibody/fluorescent antibody complexes into the optically active region (field of view) of the fiber.

In a preferred embodiment of the invention a primary antibody specific for the antigen (pathogen) to be detected is coated on a magnetic bead and a secondary antibody is conjugated to a marker. A food sample is prepared and added to the medium. If the expected pathogen, such as *Salmonella typhimurium* is present, the pathogen binds to both antibodies forming a magnetic complex. The magnetic complex is attracted to the magnetic focusing probe of the fiber-optic immunosensor containing the excitation and collecting fibers. The fibers are attached to the transmission fiber. The transmission fiber transmits the fluorescent signal received from the contacting fiber to means for detecting, collecting, and measuring the fluorescent signal. The means for detecting, collecting and measuring the fluorescent signal can be a fiber optic spectrometer in communication with a computer or a PIN detector in communication with an optical power meter.

In another aspect of the invention, a sample from the blood mammals, fish or fowl is prepared and added to a medium comprised of primary antibodies specific for the anitgens (pathogens) to be detected whereby the primary antibodies are coated on a magnetic bead and a secondary antibody conjugated to a marker. The fiber-optic immunosensor of the present invention could then be utilized as described above.

In yet another aspect of the invention, the fiber-optic immunosensor is a portable unit that can be used for field testing.

DESCRIPTION OF THE PREFERRED EMBODIMENT(S)

Figure 1:
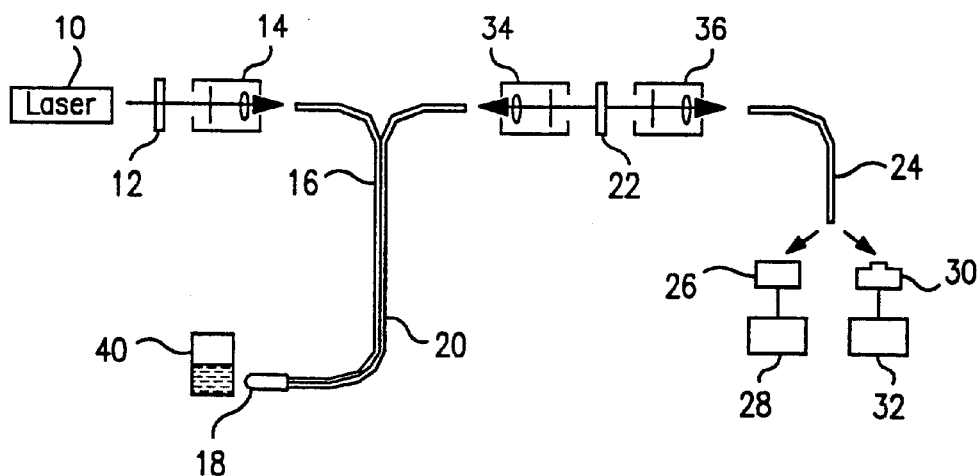
FIG. 1 is a schematic of a fiber optic immunosensor embodying the invention.

Referring to FIG. 1, a laser 10 having a 650 nm, 5-mW diode laser (Power Technology Corp.) is in communication with a line filter 12 (Omega Optical) which has its transmission maximum at 654 nm. The line filter 12 is in communication with a collimator 14 which is in communication with an exciting fiber 16. The exciting fiber 16 is in communication with a fiber optic magnetic focusing probe 18. The fiber magnetic focusing probe 18 is in communication with a collecting fiber 20. The collecting fiber 20 and the exciting fiber 16 are made from 500-micron (480-micron core) polymethyl methacrylate optical grade fibers. (ESKA brand).

The collecting fiber 20 is in communication with a collimator 34 which is in communication with a long pass filer 22. The long pass filter 22 has a cutoff of 670 nm and is made by Omega Optical. The long pass filter 22 is in communication with a transmission fiber 24 via collimator 36. The transmission fiber 24 is made of silica with a 400 micron core.

In the preferred embodiment of the invention the laser 10 is a HeNe laser with a wavelength maximum of 633 nm. The line filter 12 is omitted. The long pass filter 22 has a 50% cutoff of 664 nm. The transmission fiber 24 is in communication with a fiber optic spectrometer 26 and a computer 28. The fiber optic spectrometer 26 is an Ocean Optics (Dunedin, Fla.) model PS1000 portable spectrometer. The computer 28 is an IBM compatible computer which controls the fiber optic spectrometer 26 and collects data with the Spectro Scope ® software from Ocean Optics.

In an alternate embodiment the transmission fiber 24 is in communication with a PIN detector 30 and an optical power meter 32. The PIN detector 30 and the optical power meter 32 (Model 835) are made by Newport Corporation. The wavelength range of the CCD array in the spectrometer is 250 nm to 750 nm. The fluorescent signal from the CY5 dye is detected at approximately 674 nm. No interference is observed from the HeNe laser.

Figure 2:
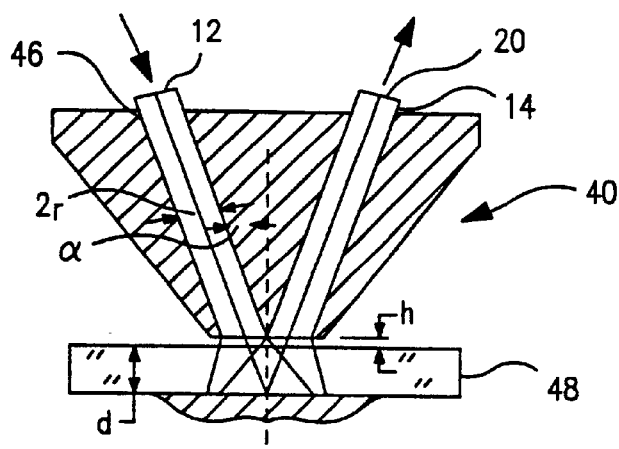
FIG. 2 is a schematic view of an embodiment of the fiber optic magnetic focusing probe of the invention.
Figure 3:
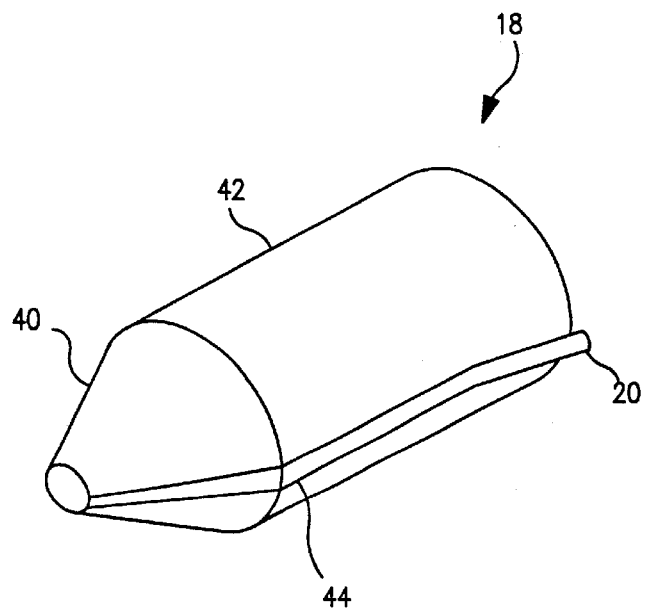
FIG. 3 is a perspective view of an embodiment of the magnetic focusing probe with parallel fibers.

Referring to FIGS. 2 and 3, a schematic and perspective view of the fiber optic magnetic focusing probe 18 is shown. The fiber optic magnetic focusing probe 18 comprises a tapered soft-iron tip 40 attached to a rare-earth permanent magnet 42 that is rated at 4600 gauss to form the probe 18. The optical fibers 16 and 20 are epoxied with a resin and secured into slits 44 and 46 that have been cut into the probe 18, 180° apart, see FIG. 3. Each optical fiber 16 and 20 is tilted at 18° from the normal to a wall 8 of a cuvette (not shown) in order to provide maximum overlap of their optical fields at the cuvette wall where the paramagnetic particles gather. The tapered soft-iron tip 40 is ground and polished and the outer edges of the tapered soft-iron tip 40 are slightly beveled so that the collection of paramagnetic particles is centered in front of the fibers. The end of the tip is about 1.2 mm in diameter. The magnet 42 has a diameter of 0.6 cm and a total length of about 3 cm.

MATERIALS AND METHODS

Materials, Chemicals, Microorganisms, and Supplies

*Salmonella typhirmium* strain ATCC 13311 was purchased from the American Type Culture Collection (Rockeville, Md.). Nutrient broth and nutrient agar were obtained from Difco laboratories (Detroit, Mich.) and used for growing and counting the Salmonella. Dynabeads® anti-Salmonella paramagnetic, spheres, 2.8 microns in diameter, were purchased from Dnyal, Inc. (Oslo, Norway). Purified (>95% IgG) polyclonal antibodies specific-to Salmonella species were obtained from Biodesign International (Kennebunk, Me.). Fluorolink-AB™ Reactive Dye labeling kits from Amersham Life Sciences Pittsburgh, Pa.) were used for labeling of the polyclonal antibodies. Fisherbrand® semi-micro disposable methacrylate cuvettes were obtained from Fisher Scientific (Springfield, N.J.). All other chemicals were ACS reagent grade. Reverse osmosis/deionized waster was used in the preparation of all solutions.

Culturing and Preparation of the Microorganisms for Assay.

Aliquots of *Salmonella typhimurium* cultures were stored at −80° C. until needed. Immunoassay cultures were prepared by thawing an aliquot of the organism and inoculating a tube of sterile nutrient broth with 1 to 2 loops of organisms. The freshly inoculated broth was then incubated at 37° C. for 9 hours. The newly grown organisms were then used immediately for the assay or stored at 4° C until they were used for the immunoassay, usually overnight. An aliquot of every freshly prepared culture was checked with the Gram staining procedure to verify the presence of *Salmonella typhimurium* and check for contaminants. The cultures were prepared for immunoassay by centrifugation at 8000×g for 15 minutes at 4° C. The spent nutrient broth was decanted and the cells were resuspended in phosphate buffered saline with 0.05% Tween 20 (PBST). An aliquot of the resuspended organisms was transferred into a vial of phosphate buffered saline (PBS) and then serially diluted in PBS for plate counts. The organisms were added to nutrient agar plates and spread on the surface and incubated at 37° C. for 24 hours for plate counts.

Immunoassay Procedures

Initially a two-step assay was run with separate steps for binding to the microspheres and labeling of the microorganisms. The organisms suspended in PBST were added to 20 $\mu$l of Dynabeads® anti-Salmonella in a microcentrifuge tube and mixed thoroughly. The mixture was mixed and incubated at room temperature for 30 minutes. After the incubation the tubes were placed into a magnetic separator and the spheres were allowed to collect on the side of the tube for 3 minutes. Then the unbound organisms in the buffer were carefully drawn from the tube, being sure not to disturb the beads collected on the sides of the tube. A 1 ml aliquot of PBST was added to the tube and thoroughly mixed. Then the tubes were placed in the magnetic separator and rinse was repeated. Each tube was rinsed 2 times. Then the spheres, with the salmonella attached were incubated with diluted secondary antibody in PBST for 30 minutes at room temperature with constant mixing. The samples were then rinsed 2 times with PBST. Finally, the microspheres with Salmonella attached were resuspended in 0.5 ml of PBST and placed into a semi-micro cuvette for the focusing assay.

For a one-step procedure the Salmonella, Dynabeads®, and CY5-IgG were combined in the microcentrifuge tube and incubated for 30 minutes at room temperature with constant mixing. Following the one-step binding and labeling procedure the tubes were placed in the magnetic separator and rinsed 2 times with PBST, and then resuspended in 0.5 ml of PBST in a semi-micro cuvette for readings with the magnetic probe. CY5-IgG solutions were diluted from 1:100 to 1:2,000 for the assays.

Results and Discussion

Preparation of secondary antibody. Conjugation of CY5 fluorescent dye with anti-Salmonella IgG. The polyclonal anti-Salmonella IgG was labeled with CY5 using the Fluorolink-Ab™ kits. Four different 1 mg aliquots of the IgG were labeled. The dye/protein ratio of the labeled IgG was calculated from the absorbance reading at 650 nm and 280 nm and the results are presented in FIG. 2. The ratios range from 5.85 to 6.92 and are consistent and with the recommended dye/protein ratios for the procedure, which are 4 to 12. A ratio less than 4 results in too little signal and greater than 12 can result in overlabeling and inactivation of the IgG and/or interference of the signal due to too much dye. A slightly higher ratio may allow for a greater dilution of the secondary antibody and may provide more sensitivity but may not be necessary.

TABLE 1

RESULTS OF CY5 CONJUGATION PROCEDURES.

| SAMPLE | DYE/PROTEIN RATIO |
|---|---|
| 1 | 5.85 |
| 2 | 6.27 |
| 3 | 6.92 |
| 4 | 6.30 |

Dilution of secondary antibody and detection of *Salmonella typhirmium*.

Magnetic Focusing of Immunoassay Samples

Figure 4:
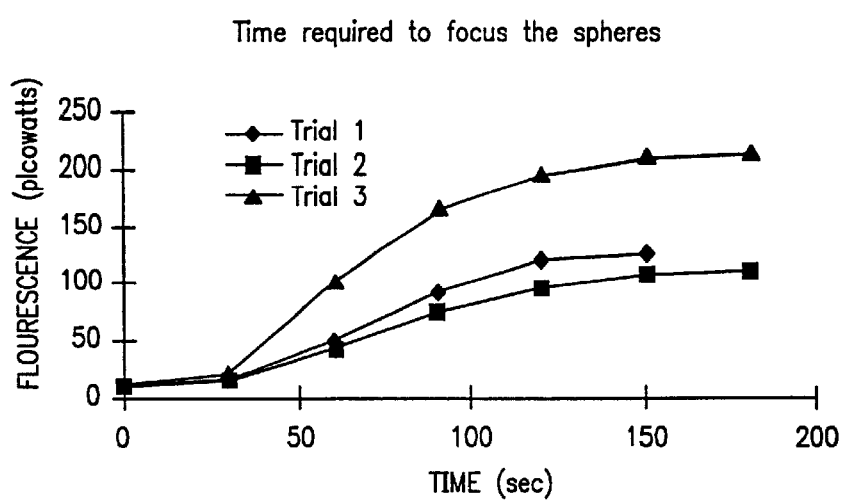
FIG. 4 is a diagram of an increase of fluorescent signals during focusing.

The one-step binding and labeling of the Salmonella procedure was used to prepare samples for the magnetic focusing trials. One-step binding and labeling of the organisms is possible due to the fact that different sources of primary and secondary antibodies were used. The primary antibody was a proprietary antibody attached to the magnetic spheres purchased from Dynal, Inc. (Oslo, Norway) and the secondary antibody purified IgG labeled with CY5 as described above. Results of the three different magnetic focusing trials are presented in FIG. 4. For trials 1 and 2 the dilution of secondary antibody was 1:500 and for Trial 3 the dilution of secondary antibody was 1:100, thus the higher signal from Trial 3 was primarily due to the difference in secondary antibody concentration. The cell concentration for Trial 1 was $2.09 \times 10^7$ CFU/ml and for Trials 2 and 3 was $1.6 \times 10_7$ CFU/ml.

The increase in signal over time demonstrates that the beads were focused in front of the magnetic fiber optic probe to enhance the detection of the organisms by separating the beads from the solution. The curve shows almost no increase in signal in first 30 seconds, followed by the most rapid increase in signal between 30 and 90 seconds, and finally a leveling off of signal at 120 seconds. No substantial increase in sensing occurred between 120 and 180 seconds. At 180 seconds the signal has reached its maximum and continued monitoring of the sample resulted only in a slight decrease as the time is extended. This may be due to bleaching of the dye due to the constant exposure to the strong laser light. Visual inspection of the cuvette after the readings are completed verified that the solution was cleared of magnetic spheres. The spheres had collected in a small, solid circle on the wall of the cuvette in front of the magnetic probe and fibers. The diameter of the circle was 3 to 5 mm.

Several factors affected the time required for focusing and the pattern and size of the beads focused on the side of the cuvette. First, the strength of the magnetic field was the most important factor in determining the time required to focus the sample. Stronger magnets resulted in shorter focusing times and complete removal of the spheres from the solutions. When weaker magnets were used the field was not strong enough to clear all of the paramagnetic spheres from solution. The strength of the magnetic field was inversely proportional to the size of the iron probe used to construct the probe. The volume and dimensions of the cuvette were also critical to the focusing step. Using the semimicro cuvettes the probe could be positioned on the side of the cuvette with the path of the cuvette no more than 5 to 6 mm from the tip of the probe. When the probe is placed in the cuvette window that allows for a 1 cm path length those spheres that are more than 5 mm to 6 mm away require much more time to focus. The end probe tip must be small to ensure that the spheres collect in front of excitation and emission fibers and form a solid, reasonably uniform layer on the side of the cuvette. The force on a paramagnet microsphere is proportional to the strength of the magnetic field and to its spatial gradient. The particles are, therefore, most strongly attracted toward the sharp corners of the magnet. When the large end of a cylindrical magnet is used, the spheres often form a ring around the outside of the magnet resulting in a large opening near the center of the magnet where the excitation and emission fibers must be located.

At 0 minutes the signal from the unfocused spheres was in the range of 9 to 12 picowatts. After the magnetic spheres were focused in front of the fibers the signal increased at least 10 fold (500×dilution of secondary IgG) to 20 fold (100×dilution of secondary IgG). Ultimately, the focusing provides a substantial advantage over reading the signal from the beads suspended in bulk solution. It also eliminates interference from the fluorescence of the unbound secondary antibody in the bulk solution.

Figure 5:
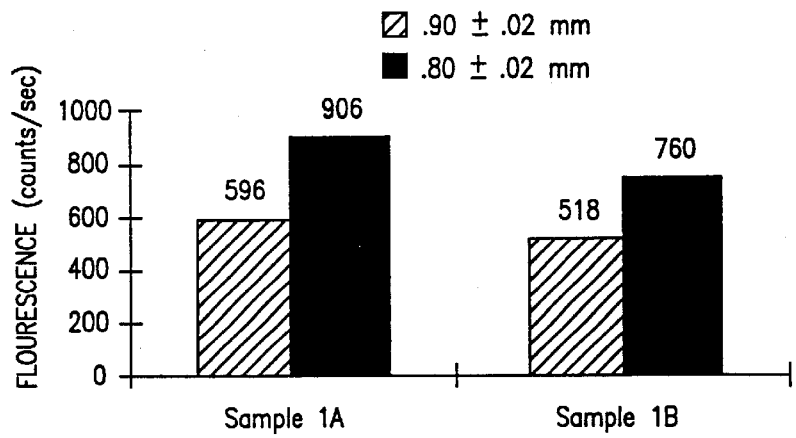
FIG. 5 is a chart of the effect of a cuvette wall thickness on the fluorescent signal.

Disposable semi-micro cuvettes were used. The thickness of the cuvette cell wall 40 was measured and it was found that for Case A the thickness was 0.90±0.02 mm and for Case B the thickness was 0.80±0.02 mm. The cuvettes were then placed in the sample holder and the signal was recorded for each case and is presented in FIG. 5. For sample 1A, the signal for case B was 52% greater than the signal for case A and for sample 1B the increase in signal was 47%. The thickness of the cuvette wall and the distance of the fibers from the paramagnetic spheres are important in obtaining consistent results.

Figure 6:
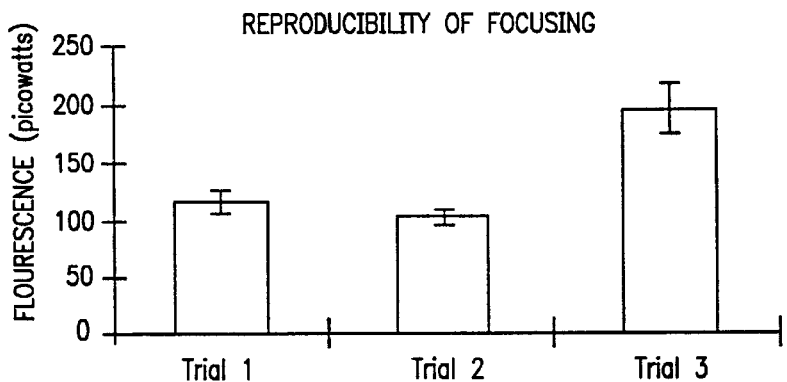
FIG. 6 is a chart on the reproducibility of the focusing step.

To test for the reproducibility of the focusing step one sample from each of the trials was inserted into the holder, focused and measured, and then removed from the holder and mixed, and then reinserted into the holder. This was repeated up to 20 times for each sample chosen. After 10 of the readings the fluorescent signal began to decrease and this was attributed to bleaching of the fluorescent dye by the laser. Consequently only data from the first 10 readings was considered valuable. FIG. 6 is a graph of the results. The difference in the absolute signal was attributed to the fact that the secondary antibody was diluted 500 fold in trials 1 and 2 and diluted 100 fold in trial 3. The error bars on the graph are the standard deviations for each sample. The % error, or coefficient of variation, for the samples was 8.0% 5.5%, and 10.6% for Trial 1, Trial 2, and Trial 3, respectively.

Variability, as measured by the coefficient of variation, due solely to the focusing step was less than 11%. An 11% error from the focusing step must be reduced and it is expected that improvements in the positioning of the cuvette, and construction of the probe are expected to decrease this error.

Figure 7:
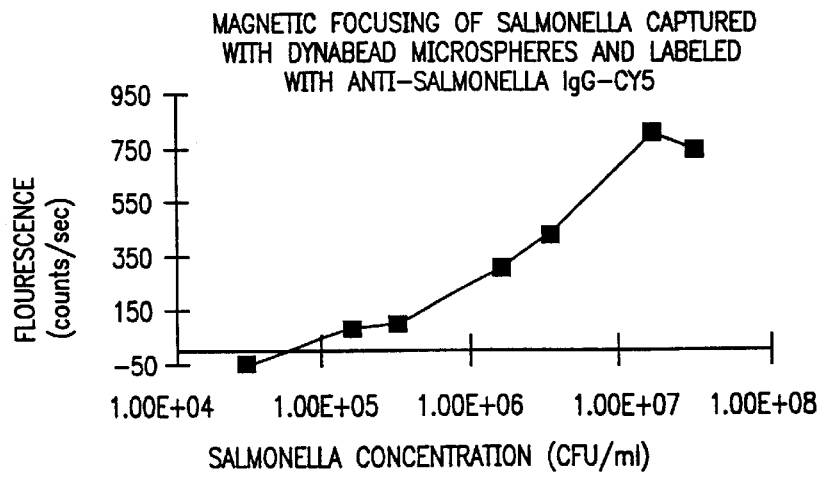
FIG. 7 is a diagram for the response of magnetically focused assay to increasing concentrations of *Salmonella typhimurium*.

Detection of *Salmonella typhimurium* with magnetically focused beads was determined by assaying a series of samples with increasing Salmonella concentrations. Three different experiments were run with increasing concentrations of Salmonella. The assay results showed that Salmonella was detected at $10^5$ CFU/ml of sample. The curve form one of these experiments is show in FIG. 7. The data show that with increasing Salmonella concentration the fluorescent signal begins to rise above the baseline at $3.17 \times 10^5$ CFU/ml and increases approximately $1.16 \times 10^7$ CFU/ml, where it reaches a maximum and levels off A two-step focusing procedure was developed to decrease analysis time. The advantage of the two-step focusing using a stronger magnet to focus the spheres on to the side of the cuvette wall prior to insertion of the curvette into the holder in front of the probe. The use of a stronger, larger magnet in the first step can reduce the total focusing time to one minute or less. The data show no difference in the quantitative results that could be attributed to the one and two-step procedures. However, one difference between one and two-step focusing is that the spot that the magnetic spheres form in front of the fiber is smaller with the two-step focusing. The two-step procedure can cut the time required to get a fluorescence reading in half.

Magnetic focusing of the spheres in front of the excitation and emission optical fibers increased the fluorescent signal several fold over the signal from the beads uniformly distributed in the bulk solution. The system proved to be very sensitive to the distance from the fibers to the layer of spheres. The process leads to an easy one or two-step focusing that will greatly simplify the measurement of Salmonella. Using the magnetic microspheres to capture the Salmonella increases the interaction of the solid phase immunoassay with the target organism. This leads to a more sensitive assay once the optimum immunoassay parameters have been defined.

Another advantage of using the magnetic focusing is that when the spheres collect in front of the fiber they form an opaque non transparent spot on the side of the cuvette. As the spheres are focused the background signal from the unbound CY5-IgG may be eliminated, or reduced to insignificant levels. This results in a very simple assay that utilizes a one-step binding and labeling step along with a one-step focusing and measurement which is a significant advancement over current procedures that require multiple incubation and rinsing steps. All the reagents can be mixed in a cuvette, or other custom designed sample holder, allowed to incubate for a specified period of time, and then measured by simply inserting the sample holder into a chamber in front of the magnetic probe.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. A method for the detection of pathogens in a sample comprising:

placing paramagnetic microspheres with immobilizing primary antibodies specific for the antigens of the pathogens in the sample;

placing optical markers bound to secondary antibodies specific for the antigens in the sample;

forming in the sample antibody/antigen/optical marker molecular complexes when pathogens are present;

subjecting the sample to a magnetic field;

concentrating in a predetermined pattern the molecular complexes in the field of view of an optically collecting fiber; and providing a signal which corresponds to the presence of the pathogens in the analyte.

2. The method of claim 1 wherein the antibodies are anti-Salmonella.

3. The method of claim 1 wherein the pathogen is *S. typhimurium*.

4. The method of claim 1 wherein the sample is blood selected from the group consisting of mammals, fish and fowl.

5. A method for the detection of pathogens in a sample comprising:

placing paramagnetic microspheres with immobilizing primary antibodies specific for the antigens of the pathogens in the sample;

placing optical markers bound to secondary antibodies specific for the antigens in the sample;

forming in the sample antibody/antigen/optical marker molecular complexes when the pathogens are present;

magnetically focusing the molecular complexes in a predetermined pattern in the field of view of an optically collecting fiber; and providing a signal which corresponds to the presence of the pathogen in the sample.

6. The method of claim 5 wherein the magnetically focusing and providing steps are substantially simultaneous.

* * * * *